(12) United States Patent
Baba

(10) Patent No.: US 10,948,708 B2
(45) Date of Patent: Mar. 16, 2021

(54) OBJECTIVE OPTICAL SYSTEM FOR ENDOSCOPE AND ENDOSCOPE

(71) Applicant: FUJIFILM Corporation, Tokyo (JP)

(72) Inventor: Tomoyuki Baba, Saitama (JP)

(73) Assignee: FUJIFILM Corporation, Tokyo (JP)

(*) Notice: Subject to any disclaimer, the term of this patent is extended or adjusted under 35 U.S.C. 154(b) by 156 days.

(21) Appl. No.: 16/214,798

(22) Filed: Dec. 10, 2018

(65) Prior Publication Data

US 2019/0187454 A1    Jun. 20, 2019

(30) Foreign Application Priority Data

Dec. 18, 2017   (JP) .............................. JP2017-242009

(51) Int. Cl.
| | | |
|---|---|---|
| *G02B 23/24* | (2006.01) | |
| *G02B 9/62* | (2006.01) | |
| *A61B 1/00* | (2006.01) | |
| *G02B 13/06* | (2006.01) | |
| *G02B 13/00* | (2006.01) | |

(52) U.S. Cl.
CPC ........ *G02B 23/243* (2013.01); *A61B 1/00096* (2013.01); *A61B 1/00174* (2013.01); *A61B 1/00188* (2013.01); *G02B 9/62* (2013.01); *G02B 13/06* (2013.01); *G02B 13/002* (2013.01); *G02B 13/0045* (2013.01)

(58) Field of Classification Search
CPC .......... G02B 23/243; G02B 9/34; G02B 9/60; G02B 9/62; G02B 9/64; G02B 23/2438; G02B 23/2415; G02B 13/0045; G02B 13/006

USPC .................................................. 359/657–660
See application file for complete search history.

(56) References Cited

U.S. PATENT DOCUMENTS

| | | | |
|---|---|---|---|
| 6,994,668 B2 | 2/2006 | Miyano | |
| 8,164,834 B2 | 4/2012 | Miyano | |
| 9,645,383 B2 | 5/2017 | Baba | |
| 2004/0125469 A1 | 7/2004 | Miyano | |
| 2009/0086017 A1 | 4/2009 | Miyano | |
| 2010/0020408 A1* | 1/2010 | Noguchi | G02B 15/173 359/676 |
| 2010/0305405 A1 | 12/2010 | Miyano | |
| 2016/0238831 A1 | 8/2016 | Baba | |
| 2017/0038563 A1* | 2/2017 | Sato | G02B 13/04 |
| 2019/0064501 A1* | 2/2019 | Katakura | A61B 1/00096 |

FOREIGN PATENT DOCUMENTS

| | | | |
|---|---|---|---|
| JP | 2596827 B2 | | 4/1997 |
| JP | 3765500 | * | 4/2006 |
| JP | 2009-080413 A | | 4/2009 |

(Continued)

*Primary Examiner* — Jordan M Schwartz
(74) *Attorney, Agent, or Firm* — Sughrue Mion, PLLC

(57) ABSTRACT

The objective optical system for an endoscope includes a negative front group, an aperture stop, and a positive rear group that are arranged in this order from an object side. The front group includes only a cemented lens in which a negative first lens, a negative second lens, and a positive third lens are cemented in this order from the object side, as a lens. The rear group includes only a cemented lens in which include a positive fourth lens, a positive fifth lens, and a negative sixth lens are cemented in this order from the object side, as a lens. Conditional expressions are satisfied.

15 Claims, 7 Drawing Sheets

EXAMPLE 1

(56) References Cited

FOREIGN PATENT DOCUMENTS

| | | |
|---|---|---|
| JP | 4265909 B2 | 5/2009 |
| JP | 2011-227380 A | 11/2011 |
| JP | 4999078 B2 | 8/2012 |
| JP | 5324321 B2 | 10/2013 |
| JP | 5363354 B2 | 12/2013 |
| JP | 2016-151629 A | 8/2016 |

* cited by examiner

EXAMPLE 1

EXAMPLE 2

EXAMPLE 3

EXAMPLE 3

OBJECTIVE OPTICAL SYSTEM FOR ENDOSCOPE AND ENDOSCOPE

CROSS-REFERENCE TO RELATED APPLICATIONS

The present application claims priority under 35 U.S.C. § 119 to Japanese Patent Application No. 2017-242009, filed on Dec. 18, 2017. The above application is hereby expressly incorporated by reference, in its entirety, into the present application.

BACKGROUND OF THE INVENTION

1. Field of the Invention

The present invention relates to an objective optical system for an endoscope and an endoscope.

2. Description of the Related Art

In the related art, endoscopes have been used for the observation, treatment, and the like for the inside of a patient's body in a medical field. JP2596827B, JP2009-080413A, JP4265909B, JP2011-227380A, JP4999078B, JP5363354B, JP5324321B, and JP2016-151629A disclose lens systems that can be used as an objective optical system for an endoscope. Each of these lens systems includes a front group having negative focal power, a stop, and a rear group having positive focal power that are arranged in this order from an object side.

SUMMARY OF THE INVENTION

For the improvement of the discovery rate of a lesion, it is required that an objective optical system for an endoscope is a wide-angle lens system capable of observing a wider range. Further, in recent years, an image taken by an endoscope has been converted into electrical signals and image processing has been performed to create an image in which blood vessels, surface structures, or the like are emphasized and to emphasize and observe a lesion portion. In such an observation, a laser source having a short wavelength near a wavelength of 400 nm (nanometer) is often used as a light source in addition to a white light source. For this reason, there is a demand for an objective optical system for an endoscope of which a chromatic aberration is corrected well in the entire range to a visible range from a short wavelength range near a wavelength of 400 nm (nanometer). Further, for a reduction in patient's burden, there is a demand for an objective optical system for an endoscope of which the outer diameter of a lens is further reduced.

However, a lateral chromatic aberration is likely to increase at a wider angle, and it is not easy to make a wide angle and the good correction of a chromatic aberration compatible with each other. It cannot be said that lens systems of examples disclosed in JP2596827B, JP2009-080413A, JP4265909B, JP2011-227380A, JP4999078B, and JP5363354B achieve an increase in an angle as wide as an angle required in recent years. Considering a range that includes a short wavelength range near a wavelength of 400 nm (nanometer), it cannot be said that an on-axis chromatic aberration and a lateral chromatic aberration of the lens system disclosed in JP5324321B are corrected well in the entire range to a visible range from this short wavelength range. The lens system disclosed in JP2016-151629A does not reach levels, which have been demanded in recent years, in terms of all items, such as an increase in angle, the good correction of a chromatic aberration, and a reduction in the outer diameter of a lens.

The invention has been made in consideration of the above-mentioned circumstances, and an object of the invention is to provide an objective optical system for an endoscope of which a chromatic aberration is corrected well at a wide angle in the entire range to a visible range from a short wavelength range near a wavelength of 400 nm (nanometer) and the outer diameter of a lens is reduced and which have high optical performance and an endoscope comprising the objective optical system for an endoscope.

In order to achieve the object, an objective optical system for an endoscope according to an aspect of the invention comprises a front group having negative focal power, an aperture stop, and a rear group having positive focal power that are arranged in this order toward an image side from an object side. The front group includes only three lenses, which consist of a first lens having negative focal power, a second lens having negative focal power, and a third lens having positive focal power arranged in this order toward the image side from the object side, as lenses. The rear group includes only three lenses, which consist of a fourth lens having positive focal power, a fifth lens having positive focal power, and a sixth lens having negative focal power arranged in this order toward the image side from the object side, as lenses. The second lens and the third lens are cemented to each other, and the fifth lens and the sixth lens are cemented to each other. Conditional expressions (1), (2), and (3) are satisfied in a case in which a composite focal length of the second and third lenses is denoted by f23, a focal length of the front group is denoted by fA, an air conversion distance between a lens surface of the third lens facing the image side and a lens surface of the fourth lens facing the object side on an optical axis is denoted by d34, a focal length of the entire system is denoted by f, a curvature radius of a lens surface of the first lens facing the image side is denoted by R2, and a curvature radius of a lens surface of the first lens facing the object side is denoted by R1.

$$-1.7 < |f23|/fA \tag{1}$$

$$0.4 < d34/R2 \tag{2}$$

$$0.8 < (1+R2/R1)/(1-R2/R1) < 1.6 \tag{3}$$

In the objective optical system for an endoscope according to the aspect of the invention, it is preferable that at least one of Conditional expression (1-1), (2-1), or (3-1) is satisfied.

$$-1.4 < |f23|/fA \tag{1-1}$$

$$0.6 < d34/R1 \tag{2-1}$$

$$0.9 < (1+R2/R1)/(1-R2/R1) < 1.2 \tag{3-1}$$

Further, in the objective optical system for an endoscope according to the aspect of the invention, it is preferable that the lens surface of the first lens facing the object side is a flat surface.

Further, in the objective optical system for an endoscope according to the aspect of the invention, in a case in which a focal length of the first lens is denoted by f1 and a focal length of the front group is denoted by fA, it is preferable that Conditional expression (4) is satisfied and it is more preferable that Conditional expression (4-1) is satisfied.

$$f1/fA<0.8 \quad (4)$$

$$f1/fA<0.5 \quad (4\text{-}1)$$

In the objective optical system for an endoscope according to the aspect of the invention, in a case in which an Abbe's number of the second lens with respect to a d line is denoted by v2 and an Abbe's number of the third lens with respect to a d line is denoted by v3, it is preferable that Conditional expression (5) is satisfied, it is more preferable that Conditional expression (5-1) is satisfied, and it is much more preferable that Conditional expression (5-2) is satisfied.

$$|v2-v3|<15 \quad (5)$$

$$|v2-v3|<10 \quad (5\text{-}1)$$

$$|v2-v3|<5 \quad (5\text{-}2)$$

In the objective optical system for an endoscope according to the aspect of the invention, in a case in which an Abbe's number of the fifth lens with respect to a d line is denoted by v5 and an Abbe's number of the sixth lens with respect to a d line is denoted by v6, it is preferable that Conditional expression (6) is satisfied and it is more preferable that Conditional expression (6-1) is satisfied.

$$41.5<|v5-v6|<80 \quad (6)$$

$$43.5<|v5-v6|<75 \quad (6\text{-}1)$$

An endoscope according to another aspect of the invention comprises the objective optical system for an endoscope according to the aspect of the invention.

"Consisting of" and "consist of" in this specification intend to include: a lens substantially not having focal power; optical elements other than the lens, such as a stop, a filter, and a cover glass; a lens flange; a lens barrel; and the like in addition to mentioned components.

In this specification, "~ group having positive focal power" means that a group has positive focal power as a whole. Likewise, "~ group having negative focal power" means that a group has negative focal power as a whole. "Single lens" means one lens that is not cemented. However, a complex aspherical lens (a lens in which a spherical lens and an aspherical film formed on the spherical lens are integrated and which functions as one aspherical lens as a whole) is treated as one lens without being regarded as a cemented lens. The sign of focal power, the curvature radius of the lens surface, and the shape of the lens surface of a lens including an aspherical surface are considered in a paraxial range unless otherwise specified. In regard to the sign of a curvature radius, the sign of the curvature radius of a surface having a convex shape toward the object side is positive and the sign of the curvature radius of a surface having a convex shape toward the image side is negative. "The entire system" means "the objective optical system for an endoscope". The "Focal length" used in conditional expressions is a paraxial focal length. The values of conditional expressions are values that are obtained in a case in which a d line is used as a reference. The "d line", "C line", "F line", and "h line" described in this specification are emission lines, and the wavelength of the d line is 587.56 nm (nanometer), the wavelength of the C line is 656.27 nm (nanometer), the wavelength of the F line is 486.13 nm (nanometer), and the wavelength of the h line is 404.66 nm (nanometer).

According to the invention, it is possible to provide an objective optical system for an endoscope of which a chromatic aberration is corrected well at a wide angle in the entire range to a visible range from a short wavelength range near a wavelength of 400 nm (nanometer) and the outer diameter of a lens is reduced and which have high optical performance and an endoscope comprising the objective optical system for an endoscope.

DESCRIPTION OF THE PREFERRED EMBODIMENTS

Figure 1:
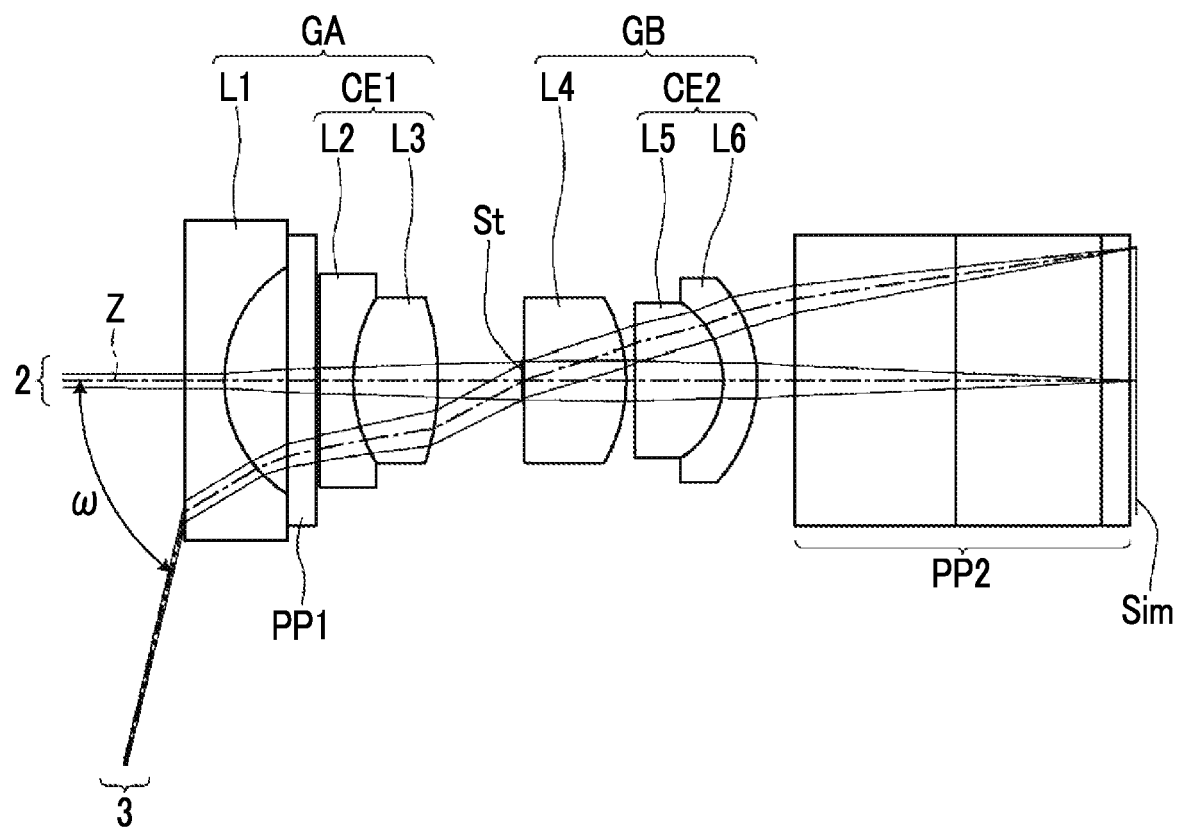
FIG. 1 is a cross-sectional view showing the configuration and optical paths of an objective optical system for an endoscope according to an embodiment of the invention (an objective optical system for an endoscope of Example 1 of the invention).

Embodiments of the invention will be described in detail below with reference to the drawings. FIG. 1 is a diagram showing the configuration and optical paths of an objective optical system for an endoscope according to an embodiment of the invention on a cross section including an optical axis Z, and corresponds to the lens configuration of Example 1 to be described later. In FIG. 1, a left side is an object side, a right side is an image side, the optical paths mean the optical path of on-axis luminous flux 2 and the optical path of luminous flux 3 corresponding to the maximum angle of view, and the half angle ω of view of the principal ray of the luminous flux 3 is also shown. ω shown in FIG. 1 corresponds to the half value of the maximum total angle of view.

The objective optical system for an endoscope according to this embodiment includes a front group GA having negative focal power, an aperture stop St, and a rear group GB having positive focal power that are arranged along the optical axis Z in this order toward the image side from the object side. Since the negative lens group and the positive lens group are arranged in this order from the object side, a retrofocus type lens system is formed. Accordingly, an optical system, which can ensure a back focus and suitably cope with a wide angle of view required for an endoscope, is formed. The aperture stop St shown in FIG. 1 does not necessarily represent a size or a shape and represents the position thereof on the optical axis Z.

The front group GA comprises only three lenses, which consist of a first lens L1 having negative focal power, a second lens L2 having negative focal power, and a third lens L3 having positive focal power arranged in this order toward the image side from the object side, as lenses. The first lens L1 is a single lens. The second lens L2 and the third lens L3 are cemented to each other and form a first cemented lens CE1. Distortion and field curvature can be suppressed by the first lens L1. Since an on-axis chromatic aberration and a lateral chromatic aberration can be suppressed by the first cemented lens CE1, it is advantageous in suppressing an on-axis chromatic aberration and a lateral chromatic aberration in the entire range to a visible range from a short wavelength range near a wavelength of 400 nm (nanometer).

It is preferable that the lens surface of the first lens L1 facing the object side is a flat surface, and the outer diameter of the first lens L1 can be reduced in this case. Further, in a case in which the lens surface of the first lens L1 facing the object side is formed of a flat surface, manufacturability can be improved and the adhesion of dust and/or liquid to the surface of the first lens L1 facing the object side can be reduced.

In the example of FIG. 1, an optical member PP1 is disposed between the first lens L1 and the second lens L2. The optical member PP1 is a member of which the incident surface and the emitting surface are parallel to each other and which does not have focal power, and is not a lens. The optical member PP1 may also be omitted in the invention. The optical member PP1 may have a filter function as necessary.

The rear group GB comprises only three lenses, which consist of a fourth lens L4 having positive focal power, a fifth lens L5 having positive focal power, and a sixth lens L6 having negative focal power arranged in this order toward the image side from the object side, as lenses. The fourth lens L4 is a single lens. The fifth lens L5 and the sixth lens L6 are cemented to each other and form a second cemented lens CE2. A spherical aberration can be suppressed by the fourth lens L4. Since a lateral chromatic aberration can be suppressed by the second cemented lens CE2, it is advantageous in suppressing a lateral chromatic aberration in the entire range to a visible range from a short wavelength range near a wavelength of 400 nm (nanometer).

In the example of FIG. 1, an optical member PP2 is disposed between the sixth lens L6 and an image plane Sim. The optical member PP2 is a member of which the incident surface and the emitting surface are parallel to each other and which does not have focal power, and is not a lens. A prism, a filter, and/or a cover glass are assumed as the optical member PP2. In a case in which a prism for bending an optical path is used as the optical member PP2, an optical path becomes a bent optical path but a drawing in which an optical path is unbent is shown in FIG. 1 for easy understanding. The optical member PP2 may also be omitted in the invention.

The objective optical system for an endoscope according to this embodiment satisfies Conditional expression (1) in a case in which a composite focal length of the second and third lenses L2 and L3 is denoted by f23 and the focal length of the front group GA is denoted by fA. f23 denotes the focal length of the first cemented lens CE1. It is possible to suppress distortion and field curvature well by making |f23| larger than the lower limit of Conditional expression (1). In addition, better characteristics can be obtained in a case in which the objective optical system for an endoscope according to this embodiment is adapted to satisfy Conditional expression (1-1).

$$-1.7<|f23|/fA \quad (1)$$

$$-1.4<|f23|/fA \quad (1\text{-}1)$$

"0≤|f23|" is satisfied since |f23| is an absolute value, and "fA<0" is satisfied since the front group GA has negative focal power. Accordingly, "|f23|/fA≤0" is satisfied.

Further, the objective optical system for an endoscope according to this embodiment satisfies Conditional expression (2) in a case in which an air conversion distance between the lens surface of the third lens L3 facing the image side and the lens surface of the fourth lens L4 facing the object side on the optical axis is denoted by d34 and the focal length of the entire system is denoted by f. It is possible to suppress astigmatism and field curvature well by making d34/f larger than the lower limit of Conditional expression (2). It is possible to suppress an increase in the entire length and the outer diameter of the optical system by making d34/f smaller than the upper limit of Conditional expression (2). In addition, better characteristics can be obtained in a case in which the objective optical system for an endoscope according to this embodiment is adapted to satisfy Conditional expression (2-1).

$$0.4<d34/f<2 \quad (2)$$

$$0.6<d34/f<1 \quad (2\text{-}1)$$

Further, the objective optical system for an endoscope according to this embodiment satisfies Conditional expression (3) in a case in which the curvature radius of the lens surface of the first lens L1 facing the image side is denoted by R2 and the curvature radius of the lens surface of the first lens L1 facing the object side is denoted by R1. It is possible to suppress distortion well by making (1+R2/R1)/(1−R2/R1) larger than the lower limit of Conditional expression (3). It is possible to reduce the outer diameter of the first lens L1 by making (1+R2/R1)/(1−R2/R1) smaller than the upper limit of Conditional expression (3). In addition, better characteristics can be obtained in a case in which the objective optical system for an endoscope according to this embodiment is adapted to satisfy Conditional expression (3-1), and much better characteristics can be obtained in a case in which the objective optical system for an endoscope according to this embodiment is adapted to satisfy Conditional expression (3-2).

$$0.8<(1+R2/R1)/(1-R2/R1)<1.6 \quad (3)$$

$$0.9<(1+R2/R1)/(1-R2/R1)<1.2 \quad (3\text{-}1)$$

$$1 \leq (1+R2/R1)/(1-R2/R1)<1.2 \quad (3\text{-}2)$$

Moreover, it is preferable that the objective optical system for an endoscope according to this embodiment satisfies Conditional expression (4) in a case in which the focal length of the first lens L1 is denoted by f1 and the focal length of the front group GA is denoted by fA. It is possible to suppress distortion and field curvature well by making f1/fA smaller than the upper limit of Conditional expression (4). Moreover, better characteristics can be obtained in a case in which the objective optical system for an endoscope according to this embodiment is adapted to satisfy Conditional expression (4-1).

$$f1/fA<0.8 \quad (4)$$

$$f1/fA<0.5 \quad (4\text{-}1)$$

"f1<0" is satisfied since the first lens L1 is a lens having negative focal power, and "fA<0" is satisfied since the front group GA has negative focal power. Accordingly, "0<f1/fA" is satisfied.

Further, it is preferable that the objective optical system for an endoscope according to this embodiment satisfies Conditional expression (5) in a case in which the Abbe's number of the second lens L2 with respect to a d line is denoted by v2 and the Abbe's number of the third lens L3 with respect to a d line is denoted by v3. It is advantageous in suppressing an on-axis chromatic aberration and a lateral chromatic aberration in the entire range to a visible range from a short wavelength range near a wavelength of 400 nm (nanometer) by making |v2−v3| smaller than the upper limit of Conditional expression (5) in the configuration of the objective optical system for an endoscope according to this embodiment. Furthermore, it is easy to use a high dispersion material having a high refractive index for both a negative lens and a positive lens of the first cemented lens CE1 by making |v2−v3| smaller than the upper limit of Conditional expression (5) in the configuration of the objective optical system for an endoscope according to this embodiment. Accordingly, since the focal power of the positive lens of the first cemented lens CE1 can be increased, it is easy to make the first cemented lens CE1 have high positive focal power and to reduce the outer diameter of the first lens L1. In addition, better characteristics can be obtained in a case in which the objective optical system for an endoscope according to this embodiment is adapted to satisfy Conditional expression (5-1), and much better characteristics can be obtained in a case in which the objective optical system for an endoscope according to this embodiment is adapted to satisfy Conditional expression (5-2).

$$|v2-v3|<15 \quad (5)$$

$$|v2-v3|<10 \quad (5\text{-}1)$$

$$|v2-v3|<5 \quad (5\text{-}2)$$

Since |v2−v3| is an absolute value and the Abbe's numbers of the negative lens and the positive lens of the cemented lens are usually different from each other, "0<|v2−v3|" is satisfied.

Further, it is preferable that the objective optical system for an endoscope according to this embodiment satisfies Conditional expression (6) in a case in which the Abbe's number of the fifth lens L5 with respect to a d line is denoted by v5 and the Abbe's number of the sixth lens L6 with respect to a d line is denoted by v6. It is advantageous in suppressing a lateral chromatic aberration in the entire range to a visible range from a short wavelength range near a wavelength of 400 nm (nanometer) by making |v5−v6| larger than the lower limit of Conditional expression (6). Since it is possible to suppress an excess of correction of a lateral chromatic aberration by making |v5−v6| smaller than the upper limit of Conditional expression (6), it is possible to optimally control a lateral chromatic aberration. Furthermore, better characteristics can be obtained in a case in which the objective optical system for an endoscope according to this embodiment is adapted to satisfy Conditional expression (6-1).

$$41.5<|v5-v6|<80 \quad (6)$$

$$43.5<|v5-v6|<75 \quad (6\text{-}1)$$

Since the above-mentioned preferred configuration and possible configurations can be randomly combined, it is preferable that the above-mentioned preferred configuration and possible configurations are appropriately selectively employed according to specifications to be required. According to this embodiment, it is possible to realize an objective optical system for an endoscope of which a chromatic aberration is corrected well at a wide angle in the entire range to a visible range from a short wavelength range near a wavelength of 400 nm (nanometer) and the outer diameter of the lens is reduced and which has high optical performance. "The outer diameter of the lens can be reduced" can be confirmed by the comparison of the outer diameters of lenses of the lens systems that are standardized depending on a focal length. "Wide angle", which is mentioned here, means that the maximum total angle of view is 150° or more.

Figure 4:
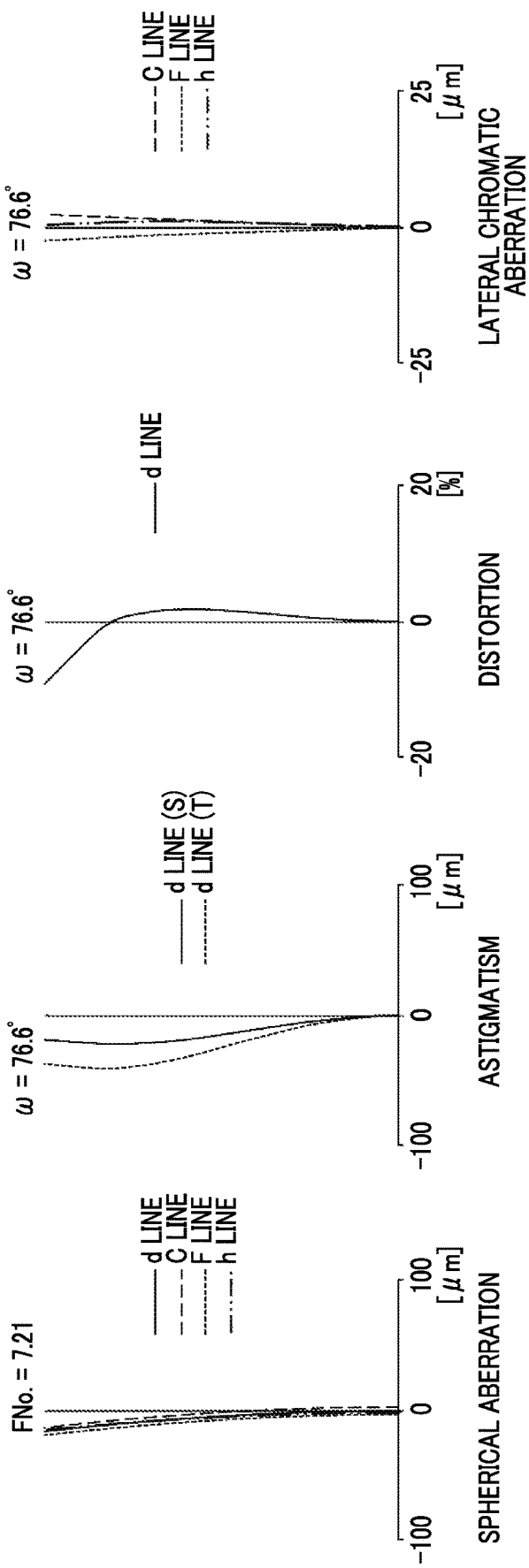
FIG. 4 is a diagram showing the respective aberrations of the objective optical system for an endoscope of Example 1 of the invention.
Figure 5:
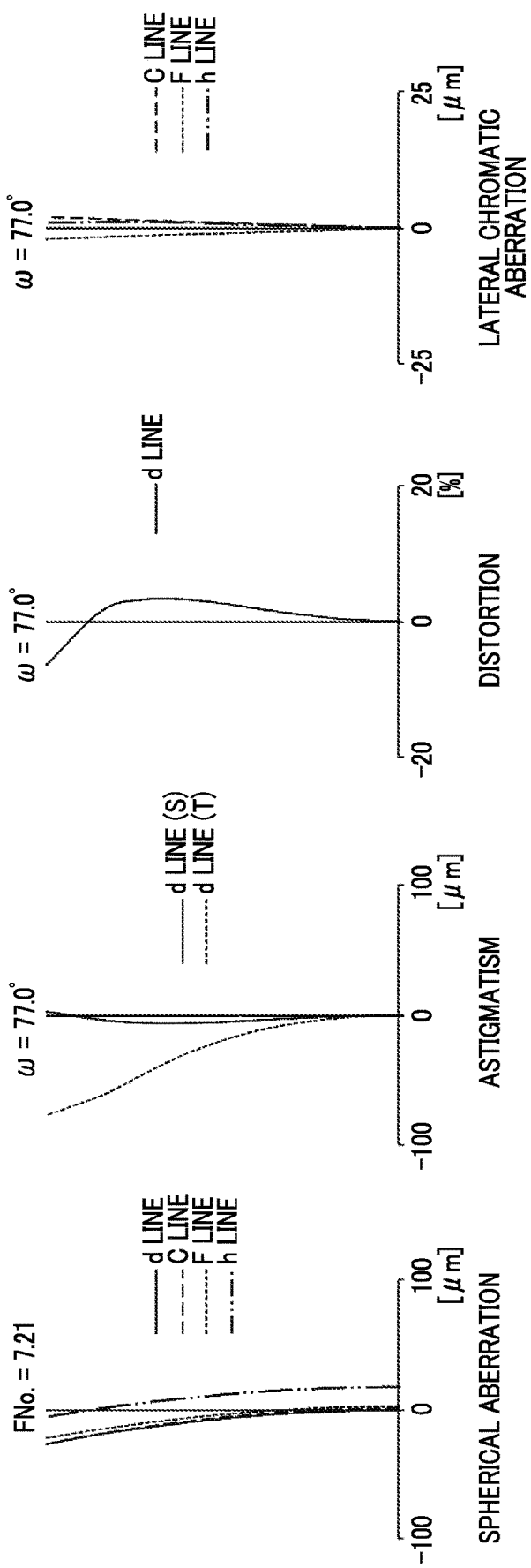
FIG. 5 is a diagram showing the respective aberrations of the objective optical system for an endoscope of Example 2 of the invention.
Figure 6:
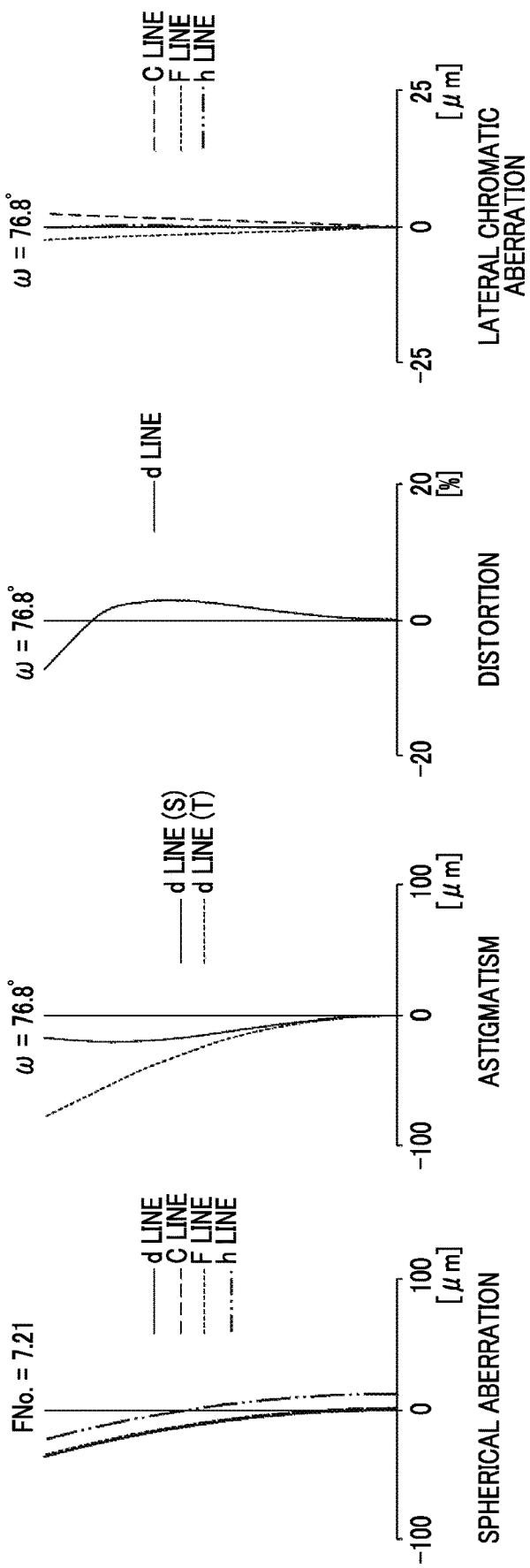
FIG. 6 is a diagram showing the respective aberrations of the objective optical system for an endoscope of Example 3 of the invention.

Next, numerical examples of the objective optical system for an endoscope according to the embodiment of the invention will be described. Basic lens data of examples to be described below and diagrams showing aberrations in FIGS. 4 to 6 are obtained in consideration of a state in which an endoscope is used in a case in which an object of which an object distance is 10 mm (millimeter) and the curvature radius of an object surface is 10 mm (millimeter) is observed.

Example 1

Since a cross-sectional view showing the configuration and optical paths of an objective optical system for an endoscope of Example 1 is shown in FIG. 1 and a showing method thereof is the same as described above, the repeated description thereof will be partially omitted here. The objective optical system for an endoscope of Example 1 includes a front group GA having negative focal power, an aperture stop St, and a rear group GB having positive focal power that are arranged in this order toward the image side from the object side. The front group GA comprises only three lenses, which consist of a first lens L1, a second lens L2, and a third lens L3 arranged in this order toward the image side from the object side, as lenses. An optical member PP1 is disposed between the first lens L1 and the second lens L2. The rear group GB consists of a fourth lens L4, a fifth lens L5, and a sixth lens L6 that are arranged in this order toward the image side from the object side. The second lens L2 and the third lens L3 are cemented to each other and form a first cemented lens CE1. The fifth lens L5 and the sixth lens L6 are cemented to each other and form a second cemented lens CE2. The above description is the summary of the objective optical system for an endoscope of Example 1.

The basic lens data of the objective optical system for an endoscope of Example 1 are shown in Table 1, and specifications thereof are shown in Table 2. In Table 1, surface numbers, which are obtained in a case in which a surface closest to the object side is set as a first surface and a number is increased toward the image side one by one, are shown in the column of Sn, the curvature radii of the respective surfaces are shown in the column of R, and a spacing between each surface and a surface adjacent to the image side on the optical axis is shown in the column of D. Further, the refractive indexes of the respective components with respect to a d line are shown in the column of Nd, and the Abbe's numbers of the respective components with respect to a d line are shown in the column of vd.

In Table 1, the sign of the curvature radius of a surface having a convex shape toward the object side is positive and the sign of the curvature radius of a surface having a convex shape toward the image side is negative. The aperture stop St, the optical member PP1, and the optical member PP2 are also shown in Table 1 together. In Table 1, the expressions of the surface number and (St) are written in the column of the surface number of a surface corresponding to the aperture stop St. A value shown in the lowest column of D in Table 1 is a spacing between the surface, which is closest to the image side, and the image plane Sim.

The value of the focal length f of the entire system and the values of the back focus Bf, the F-Number FNo., and the maximum total angle 2ω of view of the entire system at an air conversion distance are shown in Table 2 with respect to a d line. (°) in the column of 2ω means that a unit is a degree.

A degree is used as the unit of an angle and mm (millimeter) is used as the unit of a length in the data of the respective Tables, but other appropriate units can also be used since an optical system can be used even in the case of a proportional increase in size or a proportional reduction in size. Further, numerical values, which are rounded off to a predetermined place, are written in each Table to be described below.

TABLE 1

Example 1

| Sn | R | D | Nd | vd |
|---|---|---|---|---|
| OBJ | 10.00000 | 10.0000 | | |
| 1 | ∞ | 0.4000 | 1.88299 | 40.78 |
| 2 | 1.38200 | 0.6461 | | |
| 3 | ∞ | 0.3000 | 1.88299 | 40.78 |
| 4 | ∞ | 0.0350 | | |
| 5 | ∞ | 0.3500 | 2.00100 | 29.13 |
| 6 | 1.66100 | 0.8723 | 1.80518 | 25.42 |
| 7 | −2.68600 | 0.8741 | | |
| 8 (St) | ∞ | 0.0175 | | |
| 9 | ∞ | 1.0293 | 1.53775 | 74.70 |
| 10 | −1.70900 | 0.1000 | | |
| 11 | ∞ | 0.8977 | 1.43875 | 94.66 |
| 12 | −0.95300 | 0.3500 | 1.84666 | 23.78 |
| 13 | −1.53800 | 0.3947 | | |
| 14 | ∞ | 1.6500 | 1.55919 | 53.90 |
| 15 | ∞ | 1.5000 | 1.55919 | 53.90 |
| 16 | ∞ | 0.3000 | 1.51633 | 64.06 |
| 17 | ∞ | 0.0656 | | |

TABLE 2

Example 1

| f | 1.229 |
|---|---|
| Bf | 2.540 |
| FNo. | 7.21 |
| 2ω (°) | 153.2 |

A diagram showing the respective aberrations of the objective optical system for an endoscope of Example 1 is shown in FIG. 4. A spherical aberration, astigmatism, distortion, and a lateral chromatic aberration are shown in FIG. 4 in this order from the left. In the diagram showing the spherical aberration, aberrations with respect to a d line, a C line, an F line, and a h line are shown by a black solid line, a black long-dashed line, a black short-dashed line, and a black two-dot chain line, respectively. In the diagram showing the astigmatism, an aberration in a sagittal direction with respect to a d line is shown by a solid line and an aberration in a tangential direction with respect to a d line is shown by a short-dashed line, respectively. In the diagram showing the distortion, an aberration with respect to a d line is shown by a solid line. In the diagram showing the lateral chromatic aberration, aberrations with respect to a C line, an F line, and a h line are shown by a long-dashed line, a short-dashed line, and a two-dot chain line, respectively. FNo. in the diagram showing the spherical aberration means an F-Number and w in the diagrams showing the other aberrations means the half angle of view.

Since the symbols, meanings, writing methods, illustrating methods for data about Example 1 are the same as those of other examples to be described below unless otherwise specified, the repeated description thereof will be omitted below.

Example 2

Figure 2:
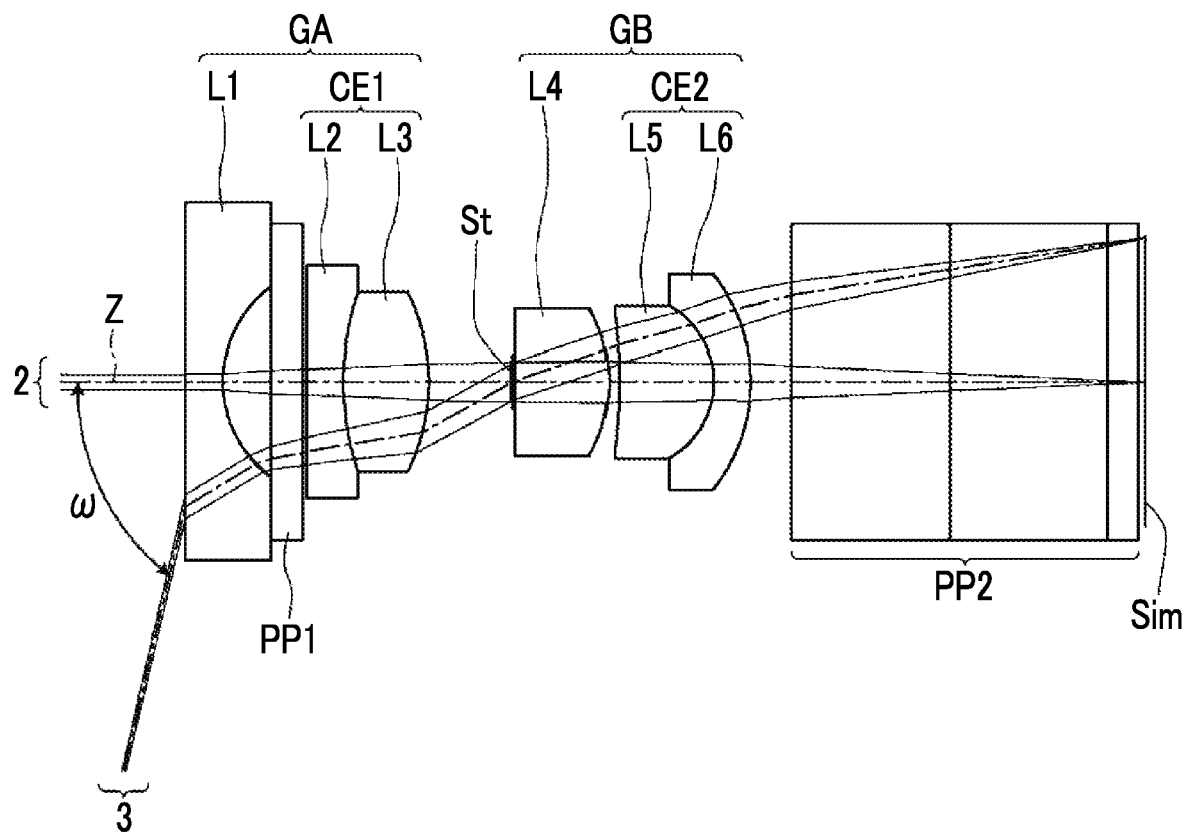
FIG. 2 is a cross-sectional view showing the configuration and optical paths of an objective optical system for an endoscope of Example 2 of the invention.

A cross-sectional view showing the configuration and optical paths of an objective optical system for an endoscope of Example 2 is shown in FIG. 2, the basic lens data thereof are shown in Table 3, the specifications thereof are shown in Table 4, and a diagram showing the respective aberrations thereof is shown in FIG. 5.

TABLE 3

Example 2

| Sn | R | D | Nd | vd |
|---|---|---|---|---|
| OBJ | 10.00000 | 10.0000 | | |
| 1 | ∞ | 0.3600 | 1.88299 | 40.78 |
| 2 | 1.12613 | 0.4582 | | |
| 3 | ∞ | 0.3000 | 1.88299 | 40.78 |
| 4 | ∞ | 0.0350 | | |
| 5 | ∞ | 0.3500 | 2.00100 | 29.13 |
| 6 | 2.69182 | 0.8085 | 1.72825 | 28.46 |
| 7 | −1.93012 | 0.7943 | | |
| 8 (St) | ∞ | 0.0175 | | |
| 9 | ∞ | 0.8925 | 1.51742 | 52.43 |
| 10 | −1.41221 | 0.1000 | | |
| 11 | −4.64158 | 0.8920 | 1.59522 | 67.73 |
| 12 | −0.83200 | 0.3500 | 1.84666 | 23.78 |
| 13 | −1.65170 | 0.3868 | | |
| 14 | ∞ | 1.5000 | 1.55919 | 53.90 |
| 15 | ∞ | 1.5000 | 1.55919 | 53.90 |
| 16 | ∞ | 0.3000 | 1.51633 | 64.06 |
| 17 | ∞ | 0.0614 | | |

TABLE 4

Example 2

| f | 1.181 |
|---|---|
| Bf | 2.440 |
| FNo. | 7.21 |
| 2ω (°) | 154.0 |

Example 3

Figure 3:
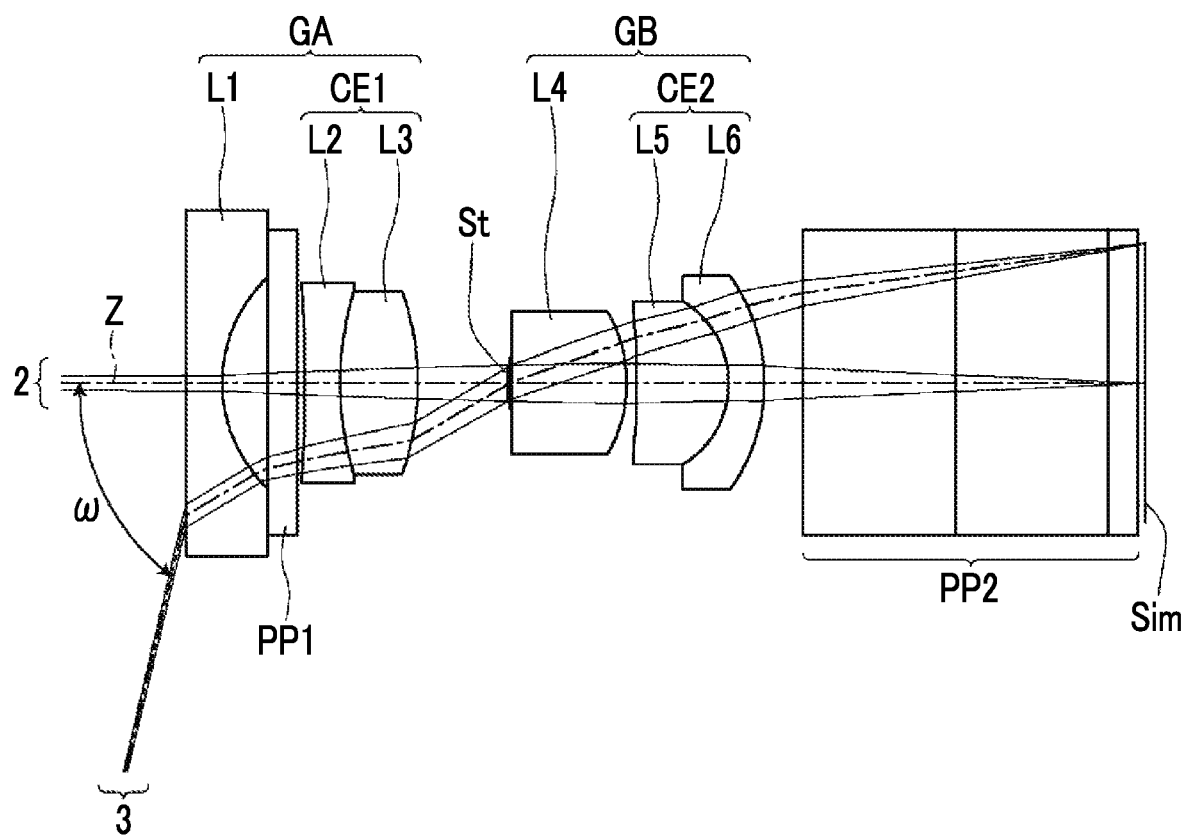
FIG. 3 is a cross-sectional view showing the configuration and optical paths of an objective optical system for an endoscope of Example 3 of the invention.

A cross-sectional view showing the configuration and optical paths of an objective optical system for an endoscope of Example 3 is shown in FIG. 3, the basic lens data thereof are shown in Table 5, the specifications thereof are shown in Table 6, and a diagram showing the respective aberrations thereof is shown in FIG. 6.

TABLE 5

Example 3

| Sn | R | D | Nd | vd |
|---|---|---|---|---|
| OBJ | 10.00000 | 10.0000 | | |
| 1 | ∞ | 0.3600 | 1.88299 | 40.78 |
| 2 | 1.42297 | 0.4443 | | |
| 3 | ∞ | 0.3000 | 1.88299 | 40.78 |
| 4 | ∞ | 0.0650 | | |
| 5 | −16.07314 | 0.3500 | 2.00100 | 29.13 |
| 6 | 3.04880 | 0.7654 | 1.78472 | 25.68 |
| 7 | −2.62277 | 0.9001 | | |
| 8 (St) | ∞ | 0.0175 | | |
| 9 | ∞ | 1.1234 | 1.51742 | 52.43 |

TABLE 5-continued

Example 3

| Sn | R | D | Nd | νd |
|---|---|---|---|---|
| 10 | −1.38660 | 0.1000 | | |
| 11 | −6.96609 | 0.9020 | 1.59522 | 67.73 |
| 12 | −0.93923 | 0.3500 | 1.84666 | 23.78 |
| 13 | −1.80168 | 0.3797 | | |
| 14 | ∞ | 1.5000 | 1.55919 | 53.90 |
| 15 | ∞ | 1.5000 | 1.55919 | 53.90 |
| 16 | ∞ | 0.3000 | 1.51633 | 64.06 |
| 17 | ∞ | 0.0688 | | |

TABLE 6

Example 3

| f | 1.198 |
|---|---|
| Bf | 2.438 |
| FNo. | 7.21 |
| 2ω (°) | 153.6 |

Values of the objective optical systems for an endoscope of Examples 1 to 3 corresponding to Conditional expressions (1) to (6) are shown in Table 7. In Examples 1 to 3, a d line is used as a reference wavelength. Table 7 shows values with respect to a d line.

TABLE 7

| Expression No. | | Example 1 | Example 2 | Example 3 |
|---|---|---|---|---|
| (1) | \|f23\|/fA | −1.098 | −0.548 | −1.360 |
| (2) | d34/f | 0.726 | 0.688 | 0.766 |
| (3) | (1 + R2/R1)/(1 − R2/R1) | 1.000 | 1.000 | 1.000 |
| (4) | f1/fA | 0.342 | 0.206 | 0.407 |
| (5) | \|ν2 − ν3\| | 3.71 | 0.67 | 3.45 |
| (6) | \|ν5 − ν6\| | 70.88 | 43.96 | 43.96 |

As known from the above-mentioned data, according to the objective optical systems for an endoscope of Examples 1 to 3, the maximum total angle of view is a wide angle of 150° or more, a chromatic aberration in the entire range to a visible range from a short wavelength range near a wavelength of 400 nm (nanometer) is corrected well, other aberrations are also corrected well, the outer diameter of the lens is reduced, and high optical performance is achieved.

Figure 7:
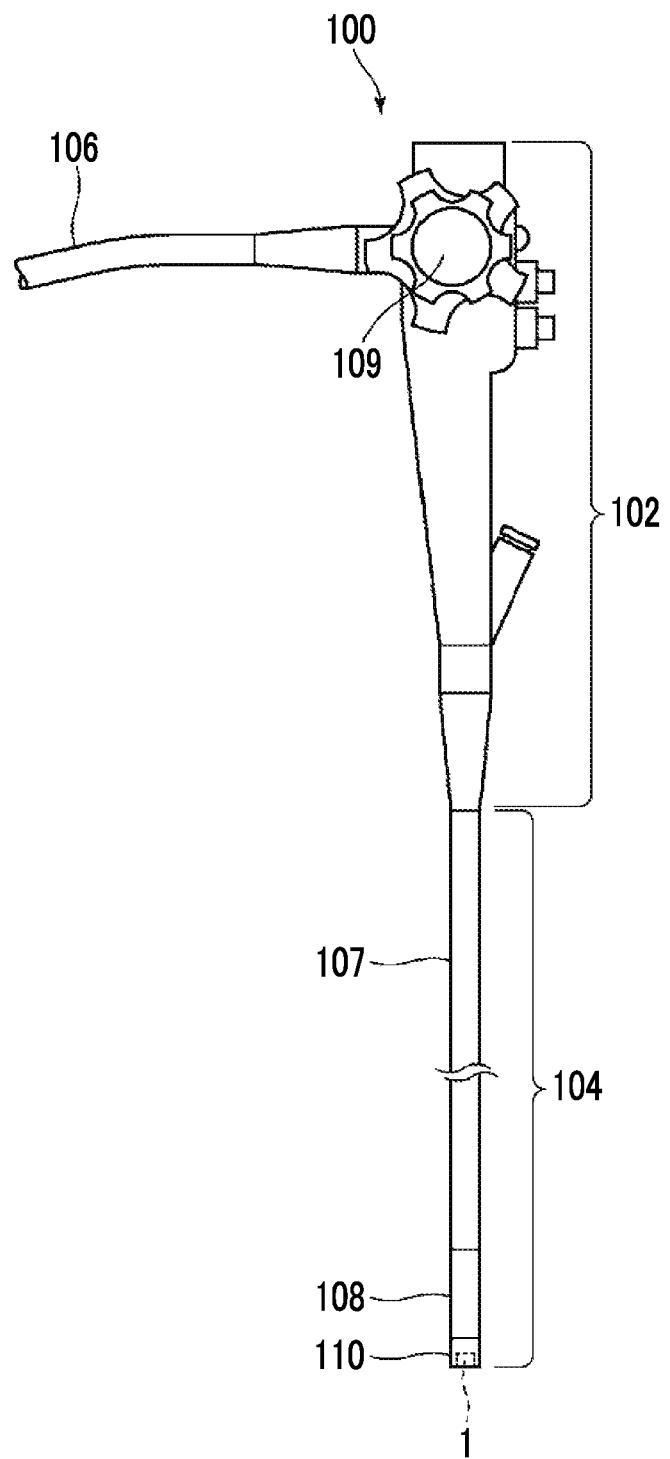
FIG. 7 is a diagram showing the schematic configuration of an endoscope according to an embodiment of the invention.

Next, an endoscope according to an embodiment of the invention will be described. A diagram showing the entire schematic configuration of an endoscope according to an embodiment of the invention is shown in FIG. 7. The endoscope 100 shown in FIG. 7 mainly comprises an operation unit 102, an insertion part 104, and a universal cord 106 that is to be connected to a connector part (not shown). A large portion of the insertion part 104 is a soft portion 107 that is bendable in any direction along an insertion path, a bendable portion 108 is connected to the distal end of the soft portion 107, and a distal end portion 110 is connected to the distal end of the bendable portion 108. The bendable portion 108 is provided to allow the distal end portion 110 to turn in a desired direction, and can be operated to be bent by the rotational movement of a bending operation knob 109 provided on the operation unit 102. An objective optical system 1 for an endoscope according to the embodiment of the invention is provided in the distal end of the distal end portion 110. The objective optical system 1 for an endoscope is schematically shown in FIG. 7.

Since the endoscope according to this embodiment comprises the objective optical system for an endoscope according to the embodiment of the invention, the diameter of the insertion part 104 can be reduced and the endoscope can make an observation with a wide angle of view. Further, since the endoscope can acquire a good image in the entire range to a visible range from a short wavelength range near a wavelength of 400 nm (nanometer), the endoscope can be suitably applied to the observation of an image in which blood vessels, surface structures, or the like are emphasized and which is obtained from the combination of the use of white light and a laser beam having a wavelength of about 400 nm (nanometer) and image processing.

The invention has been described above using the embodiments and the examples, but the invention may have various modifications without being limited to the embodiments and the examples. For example, the curvature radius, the surface spacing, the refractive index, and the Abbe's number of each lens may have other values without being limited to values shown in the respective numerical examples.

What is claimed is:

1. An objective optical system for an endoscope comprising a front group being the most front group in the objective optical system and having negative focal power, an aperture stop, and a rear group being the most rear group in the objective optical system and having positive focal power that are arranged in this order toward an image side from an object side, wherein the front group has only three lenses, which consist of a first lens having negative focal power, a second lens having negative focal power, and a third lens having positive focal power arranged in this order toward the image side from the object side, as lenses, the rear group has only three lenses, which consist of a fourth lens having positive focal power, a fifth lens having positive focal power, and a sixth lens having negative focal power arranged in this order toward the image side from the object side, as lenses, the second lens and the third lens are cemented to each other, the fifth lens and the sixth lens are cemented to each other, and Conditional expressions (1-1), (2a), and (3) are satisfied wherein a composite focal length of the second and third lenses is denoted by f23, a focal length of the front group is denoted by fA, an air conversion distance between a lens surface of the third lens facing the image side and a lens surface of the fourth lens facing the object side on an optical axis is denoted by d34, a focal length of the objective optical system for an endoscope is denoted by f, a curvature radius of a lens surface of the first lens facing the image side is denoted by R2, and a curvature radius of a lens surface of the first lens facing the object side is denoted by R1, $$1.4 < |f23|/fA \quad (1\text{-}1)$$

$$0.6 < d34/f < 2 \quad (2a)$$

$$0.8 < (1+R2/R1)/(1-R2/R1) < 1.6 \quad (3).$$

2. The objective optical system for an endoscope according to claim 1, wherein the lens surface of the first lens facing the object side is a flat surface.

3. The objective optical system for an endoscope according to claim 1,
wherein Conditional expression (4) is satisfied wherein a focal length of the first lens is denoted by f1, $$f1/fA < 0.8 \tag{4}$$

4. The objective optical system for an endoscope according to claim 1,
wherein Conditional expression (5) is satisfied wherein an Abbe's number of the second lens with respect to a d line is denoted by v2 and an Abbe's number of the third lens with respect to a d line is denoted by v3, $$|v2-v3| < 15 \tag{5}$$

5. The objective optical system for an endoscope according to claim 1,
wherein Conditional expression (6) is satisfied wherein an Abbe's number of the fifth lens with respect to a d line is denoted by v5 and an Abbe's number of the sixth lens with respect to a d line is denoted by v6, $$41.5 < |v5-v6| < 80 \tag{6}$$

6. The objective optical system for an endoscope according to claim 1,
wherein Conditional expression (2-1) is satisfied, $$0.6 < d34/f < 1 \tag{2-1}$$

7. The objective optical system for an endoscope according to claim 1,
wherein Conditional expression (3-1) is satisfied, $$0.9 < (1+R2/R1)/(1-R2/R1) < 1.2 \tag{3-1}$$

8. The objective optical system for an endoscope according to claim 3,
wherein Conditional expression (4-1) is satisfied, $$f1/fA < 0.5 \tag{4-1}$$

9. The objective optical system for an endoscope according to claim 4,
wherein Conditional expression (5-1) is satisfied, $$|v2-v3| < 10 \tag{5-1}$$

10. The objective optical system for an endoscope according to claim 4,
wherein Conditional expression (5-2) is satisfied, $$|v2-v3| < 5 \tag{5-2}$$

11. The objective optical system for an endoscope according to claim 5,
wherein Conditional expression (6-1) is satisfied, $$43.5 < |v5-v6| < 75 \tag{6-1}$$

12. An endoscope comprising:
the objective optical system for an endoscope according to claim 1.

13. An objective optical system for an endoscope comprising
a front group being the most front group in the objective optical system and having negative focal power, an aperture stop, and a rear group being the most rear group in the objective optical system and having positive focal power that are arranged in this order toward an image side from an object side,
wherein the front group has only three lenses, which consist of a first lens having negative focal power, a second lens having negative focal power, and a third lens having positive focal power arranged in this order toward the image side from the object side, as lenses,
the rear group has only three lenses, which consist of a fourth lens having positive focal power, a fifth lens having positive focal power, and a sixth lens having negative focal power arranged in this order toward the image side from the object side, as lenses,
the second lens and the third lens are cemented to each other,
the fifth lens and the sixth lens are cemented to each other, and
Conditional expressions (1), (2), and (3) are satisfied wherein a composite focal length of the second and third lenses is denoted by f23, a focal length of the front group is denoted by fA, an air conversion distance between a lens surface of the third lens facing the image side and a lens surface of the fourth lens facing the object side on an optical axis is denoted by d34, a focal length of the objective optical system for an endoscope is denoted by f, a curvature radius of a lens surface of the first lens facing the image side is denoted by R2, and a curvature radius of a lens surface of the first lens facing the object side is denoted by R1, $$-1.7 < |f23|/fA \tag{1}$$

$$0.4 < d34/f < 2 \tag{2}$$

$$0.8 < (1+R2/R1)/(1-R2/R1) < 1.6 \tag{3},$$

wherein an Abbe's number of the second lens with respect to a d line is denoted by v2 and an Abbe's number of the third lens with respect to a d line is denoted by v3,
wherein Conditional expression (5-1) is satisfied, $$|v2-v3| < 10 \tag{5-1}$$

14. The objective optical system for an endoscope according to claim 13,
wherein Conditional expression (5-2) is satisfied, $$|v2-v3| < 5 \tag{5-2}$$

15. An endoscope comprising:
the objective optical system for an endoscope according to claim 13.

* * * * *